United States Patent [19]

Sauers

[11] Patent Number: 4,633,082
[45] Date of Patent: Dec. 30, 1986

[54] PROCESS FOR MEASURING DEGRADATION OF SULFUR HEXAFLUORIDE IN HIGH VOLTAGE SYSTEMS

[75] Inventor: Isidor Sauers, Knoxville, Tenn.

[73] Assignee: The United States of America as represented by the United States Department of Energy, Washington, D.C.

[21] Appl. No.: 726,564

[22] Filed: Apr. 23, 1985

[51] Int. Cl.⁴ .............................................. B01D 59/44
[52] U.S. Cl. .................................... 250/282; 250/288; 250/423 P
[58] Field of Search ............. 250/281, 282, 288, 423 P

[56] References Cited

U.S. PATENT DOCUMENTS

| | | | |
|---|---|---|---|
| 3,626,181 | 12/1971 | Wermland | 250/282 |
| 3,742,213 | 6/1973 | Cohen et al. | 250/282 |
| 3,920,987 | 11/1975 | Anbar et al. | 250/282 |
| 4,158,775 | 6/1979 | Chutjion et al. | 250/282 |
| 4,401,920 | 8/1983 | Taylor | 250/423 P |

*Primary Examiner*—Bruce C. Anderson
*Attorney, Agent, or Firm*—Katherine P. Lovingood; Stephen D. Hamel; Judson R. Hightower

[57] ABSTRACT

This invention is a method of detecting the presence of toxic and corrosive by-products in high voltage systems produced by electrically induced degradation of $SF_6$ insulating gas in the presence of certain impurities. It is an improvement over previous methods because it is extremely sensitive, detecting by-products present in parts per billion concentrations, and because the device employed is of a simple design and takes advantage of the by-products natural affinity for fluoride ions. The method employs an ion-molecule reaction cell in which negative ions of the by-products are produced by fluorine attachment. These ions are admitted to a negative ion mass spectrometer and identified by their spectra. This spectrometry technique is an improvement over conventional techniques because the negative ion peaks are strong and not obscured by a major ion spectra of the $SF_6$ component as is the case in positive ion mass spectrometry.

2 Claims, 5 Drawing Figures

TO MASS SPECTROMETER

PROCESS FOR MEASURING DEGRADATION OF SULFUR HEXAFLUORIDE IN HIGH VOLTAGE SYSTEMS

BACKGROUND OF THE INVENTION

This invention relates generally to early detection of toxic and corrosive by-products formed by electrical discharges in some high voltage systems and more specifically to an ion-molecule reaction cell and negative ion mass spectrometry method for detecting by-products that result from degradation of sulfur hexafluoride, a gas insulator, and is a result of a contract with the United States Department of Energy.

Sulfur hexafluoride, $SF_6$, is a gas used as an insulator in conjunction with solid insulating material in high voltage systems such as transmission lines, substations and switchgear. In the course of operating such high voltage systems electrical discharges can occur in the form of coronas, arcs or sparks. If there are no impurities present in the system, only $SF_6$, then $SF_6$ attaches to electrons to form $SF_6^-$ or $SF_6$ could degrade to $SF_4$ and fluorine (F or $F_2$). In either case an equilibrium is established between $SF_6$ and $SF_6^-$ or $SF_4$ and F or $F_2$. However, if there are impurities in the system the $SF_6$ can further degrade eventually resulting in voltage breakdown. In the presence of oxygen or water from atmospheric moisture, silicon from lubricants and insulators, and tungsten from electrode materials, gaseous by-products are produced that can be toxic and corrosive. These by-products include $SiF_4$, $SOF_4$, $SO_2F_2$, $SO_2$, $SOF_2$, $WF_6$, $SF_4$, F, $F_2$ and HF.

Conventional methods for detecting these by-products include electron impact mass spectrometry (MS), gas chromatography (GC) with thermal conductivity detection, gas chromatography with electron capture detection, and a combination of gas chromatography and mass spectrometry. Conventional electron impact mass spectrometry has limited use since the mass spectra are dominated by the $SF_6$ ion peaks, obscuring the ion peaks representative of the $SF_6$ by-products. GC with thermal conductivity detection has sensitivities of only about 100 ppm. GC with electron capture detection is not suitable for some of the by-products since they are not good electron attachers and must compete with the strongly electron attaching $SF_6$; for example, $SiF_4$ does not attach low energy electrons and only weakly attaches electrons at high electron energies (~10 ev). Combination GC/MS has the problem of complex spectra and low sensitivity (~1 ppm). An analytical method that detects the presence of degradation produced by-products in the parts per billion (ppb) level would be preferable.

This invention detects these by-products at very low concentrations (ppb) using an ion-molecule reaction cell and a negative ion mass spectrometer. The ion-molecule reaction cell has previously been used in electron attachment studies that were limited to studying parent ions but were not used to generate ions other than the parent ions, as is done in this invention. Negative ion mass spectrometry has not been previously used to detect by-products of $SF_6$ degradation because generation of negative ions of the by-products has not been previously done.

There is a need to detect the formation of impurities as early as possible, preferably in the ppb range since prolonged buildup can result in degradation of $SF_6$ and attendant high voltage breakdown and also because the by-products formed in the degradation process are, for the most part, toxic and corrosive, posing a hazard to system operators.

SUMMARY OF THE INVENTION

In view of the above-mentioned needs, it is an object of this invention to provide a process for early detection of degradation of $SF_6$ in high voltage systems.

It is another object of this invention to provide a device that detects by-products of degradation of $SF_6$ in the ppb range.

It is a further object of this invention to avoid the buildup of toxic and corrosive substances in high voltage systems.

Another object of this invention is to avoid high voltage breakdown caused by degradation of $SF_6$.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, the process of this invention comprises placing $SF_6$ gas to be tested in an ion-molecule reaction cell with a cathode at one end and an anode at the opposite end, producing thermal electrons at the cathode in the reaction chamber thus ionizing the gas molecules in the vicinity of the cathode, applying an electrical field in the reaction cell to permit transfer of ions from the cathode to the anode, passing the ions through a pin hole aperture located in the vicinity of the anode from the high pressure reaction chamber into a low pressure negative ion mass spectrometer, and detecting the identity of the negative ions.

In the preferred embodiment the pressure should be sufficiently high so that an optimum number of the electrons are scavenged by electron attachment to $SF_6$, generally in the range of 0.1 to 800 torr, depending on the concentration of ions present in the gas. The production of the low energy thermal electrons is preferably done by using a mercury vapor ultraviolet light source that emits photons which pass through a quartz window and impinge on a thin cathode film of a low work function material such as palladium or gold. Other sources such as a corona or beta radioactive source may be used to produce electrons; however, these other sources tend to have much broader electron energy distributions, which result in a more complicated ion spectrum. There is an electrical connection to the thin metallic film so the film also acts as the cathode. The anode is preferably at ground potential.

The preferred method of detecting the identity of the negative ions that reach the anode is by negative ion mass spectrometer. Using this method, there is at the anode a pin hole aperture that permits escape of the negative ions from the reaction chamber into the negative ion mass spectrometer that is able to detect the presence of ionic by-products in the ppb range.

Another method of detecting the identity of the ions would utilize the mobilities of the respective ions. If the time necessary for an ion to traverse the reaction cell is known, identity could be determined based on known mobilities rather than using the mass spectrometer.

Formation of the ionic by-products under pressure and the use of negative ion mass spectrometry have advantages over previous methods because by-products can be detected in the parts per billion range. Having the reaction chamber at higher pressure increases the density of these minor components thereby optimizing the number of ions formed while the negative ion mass spectrometer has the advantage of being able to detect the peaks of these minor components without them being obscured by the peak of a major component, as is the case in conventional electron impact mass spectrometry.

DETAILED DESCRIPTION OF THE PREFERRED EMBODIMENT

Due to its excellent electron attaching properties, sulfur hexafluoride ($SF_6$) is used as a gas insulator in high voltage equipment such as transmission lines, substations and switchgear. When electrical discharges occur in the form of sparks, coronas and arcs, $SF_6$ can capture these electrons resulting in $SF_6^-$ ions, or it can degrade to sulfur tetrafluoride ($SF_4$) and fluorine (F or $F_2$), both of which are reversible processes in the absence of impurities.

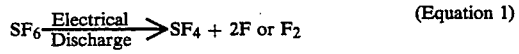

(Equation 1)

However, in the presence of impurities further reactions take place that prevent the reformation of $SF_6$, and after continued reactions of this nature, $SF_6$ will eventually degrade to the extent that voltage breakdown will occur and the $SF_6$ no longer functions as an insulator. Impurities that can be present in these systems include oxygen ($O_2$), water ($H_2O$), silicon (Si) and tungsten (W). The formation of $SF_4$ and F from an electrical discharge (Equation 1) can further result in reactions between $SF_4$ and impurities to form by-products as shown generally (not intended to be balanced equations) as follows:

| Impurities | By-Products |
|---|---|
| $SF_4 \xrightarrow{H_2O \text{ or } O_2}$ | $SO_2F_2$ |
| | $SOF_4$ |
| | $SOF_2$ |
| | HF |
| | $SO_2$ |
| $SF_4 \xrightarrow{Si}$ | $SiF_4$ |
| $SF_4 \xrightarrow{W}$ | $WF_6$ |

Detection of the presence of these by-products at extremely low concentrations (ppb) is the essence of this invention.

The process of detection is based primarily on two reactions: (1) electron attachment to $SF_6$ (Equation 2); and (2) fluoride exchange reaction (Equation 3)

(Equation 2)

(Equation 3)

where X denotes by-products formed as a result of electrical discharge in the presence of $SF_6$ and impurities that have higher fluoride affinities than $SF_5$.

The gas insulation is removed from the high voltage system using known methods and placed in a high pressure reaction cell. Low energy electrons are produced at a first end of the reaction cell, thereby ionizing $SF_6$ to form $SF_6^-$ (Equation 2). The by-products X present as a result of $SF_6$ degradation in the high voltage system undergo fluoride exchange reactions (Equation 3) to produce the $XF^-$ ions that can be detected by negative ion mass spectrometry. The ions are transported to the second end of the reaction cell opposite the first end by employing an applied electric field. At the second end is a pin hole aperture that permits the gas to exit the reaction cell and enter the negative ion mass spectrometer where detection takes place.

Figure 1:
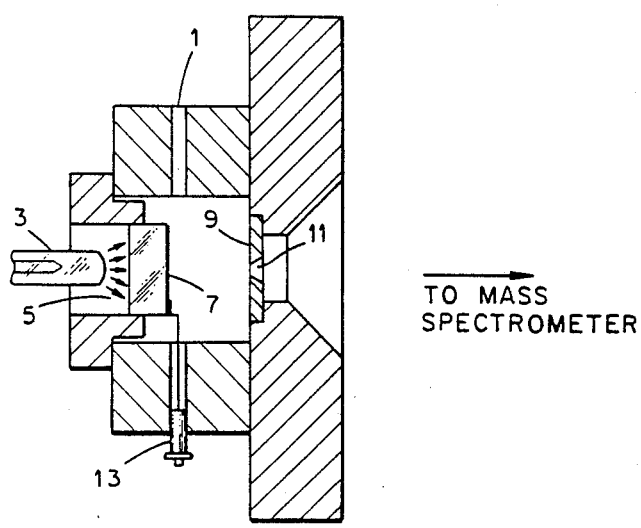
FIG. 1 is a schematic drawing of the ion-molecule reaction cell.

The ion-molecule reaction cell where the negative ions are formed is represented by the schematic drawing of FIG. 1. A sample of the gas to be tested is admitted to the cell through the gas inlet 1 and is maintained at sufficient pressure to ensure electron attachment to $SF_6$ (0.1 to 800 torr). A mercury vapor ultraviolet light source 3 emit thermal electrons (photons) that pass through a quartz window 5 and impinge on a thin film 7 of low work function material such as palladium or gold producing low energy electrons by photoemission resulting in formation of negative ions. An electrical connection 13 is provided to the thin metallic film so that the window also serves as a cathode. The opposing anode surface 9 incorporates a sampling aperture 11 to permit ions formed in the reaction cell to drift into the mass spectrometer (not shown).

When $SF_6$ is the major component of the gas, low energy electrons produced at the cathode are quickly attached near the cathode (Equation 2) forming $SF_6^-$ since the thermal electron attachment rate for $SF_6^-$ formation is high ($k_a \sim 2 \times 10^{-7}$ cm$^3$s$^{-1}$). As these ions drift the length of the cell the by-products X (formed from electrical discharges in the presence of impurities in the high voltage system), having a higher fluorine affinity than $SF_5$ accept fluoride ions from the $SF_6^-$ thereby forming $XF^-$ ions (Equation 3). These ions travel through the pin hole aperture at the anode into the negative ion mass spectrometer for detection.

In general, the density $n_x$ of the trace by-product X is determined only from the intensities $I_{XF^-}$ and $I_{SF_6^-}$ of the ions $XF^-$ and $SF_6^-$ by the expression (ignoring mass discrimination effects, which should be negligible over the small mass difference generally encountered)

$$n_x = \frac{-\ln[I_{SF_6^-}/(I_{XF^-} + I_{SF_6^-})]}{k_x t_r}$$

(Equation 4)

where $k_x$ is the rate constant for the reaction of Equation 3 and $t_r$ is the reaction time determined by $$t_r = \frac{d}{V_d} \text{ and} \qquad \text{(Equation 5)}$$

$$V_d = 836 \, E/P \text{ where} \qquad \text{(Equation 6)}$$

d is the drift distance, $\mu$ is the mobility of $SF_6^-$ in $SF_6$ and E/P is the pressure normalized electric field. Values of $\mu$ for $SF_6^-$ can be found in the literature. The rate constants $k_x$ can be established from Equations 4–6 by admitting into the reaction cell a known density $n_x$ of gas X. Table I gives the ions and rate constants determined by this method.

TABLE I

| Molecule X | Neg. Ion | k (cm$^3$/s) |
|---|---|---|
| $SOF_4$ | $SOF_5^-$ | $2 \times 10^{-10}$ |
| $SiF_4$ | $SiF_5^-$ | $1 \times 10^{-9}$ |
| $SF_4$ | $SF_5^-$ | $3 \times 10^{-10}$ |
| $WF_6$ | $WF_7^-$ | $3 \times 10^{-10}$ |

The method for determining $n_x$ is, therefore, independent of the electron current, the $SF_6^-$ ion intensity and the absolute pressure. It depends only on the ratio of ion currents $I_{SF_6^-}/I_{XF^-} + I_{SF_6^-}$).

The potential for ultra high sensitivity is demonstrated by the following calculations: for detection of $SiF_4$ at E/P 10 v/cm torr and assuming $I_{SiF_5^-}/I_{SF_6^-} \sim 10^{-3}$), (reasonable since $SF_6^-$ ion intensities of $10^4$ s$^{-1}$ is curruntly achieved with the mercury discharge lamp, thereby requiring $I_{SiF_5^-} \sim 10$ s$^{-1}$), then for a total pressure of 100 torr and a drift distance of 4 cm the minimum density $n_x$ detectable is $$n_x \sim \frac{-\ln 0.999}{(10^{-9} \text{cm}^3/s^{-1})(10^{-3} s)} \sim 10^9 \text{ cm}^{-3}$$

thus at P=100 torr the minimum concentration detectable is $$n_x/n_{SF_6} \sim \frac{10^9}{3 \times 10^{18}} \sim 3 \times 10^{-10}$$

or in the 300 parts per trillion range.

Thus, sensitivity is most impressive and even greater sensitivity can be achieved with higher pressures, longer drift distances, higher ion intensities, increased lamp output and optimization of film thickness of the electron-emitting coating.

EXAMPLE

Figure 3:
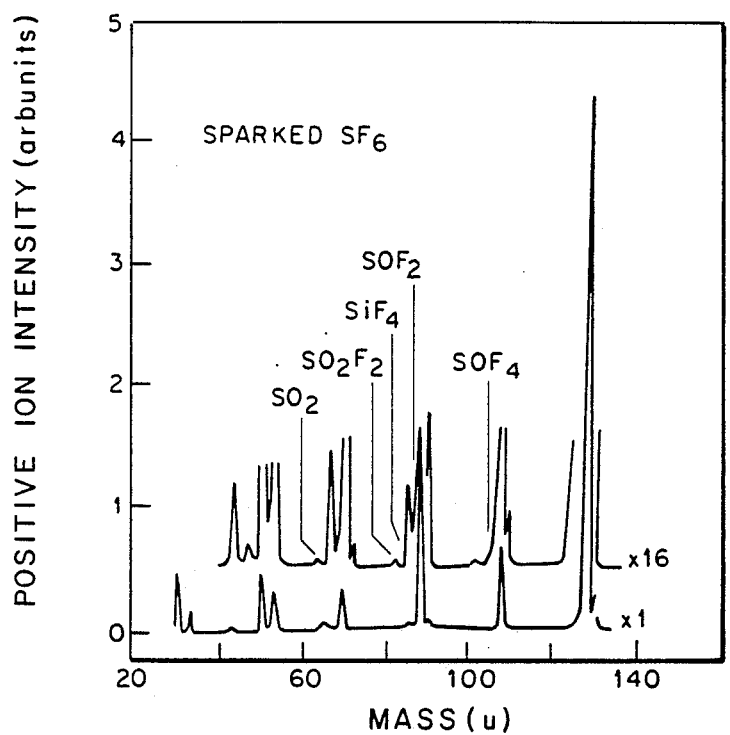
FIG. 3 is the positive ion electron impact mass spectrum of sparked $SF_6$ sample at low sensitivity (X1) and high sensitivity (X16)
Figure 2A:
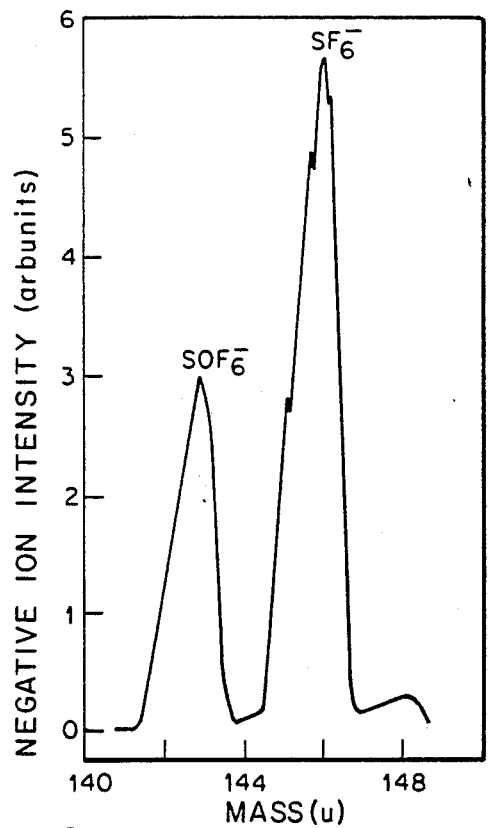
FIG. 2 is negative ion spectra for 0.1 percent $SOF_4$ in $SF_6$ at $P = 133$ Pa and E/N (density normalized electric field, which determines electron energy distribution function)$\simeq$(a) $12 \times 10^{-16}$ and (b) $4.9 \times 10^{-16}$ V cm$^2$.
Figure 2B:
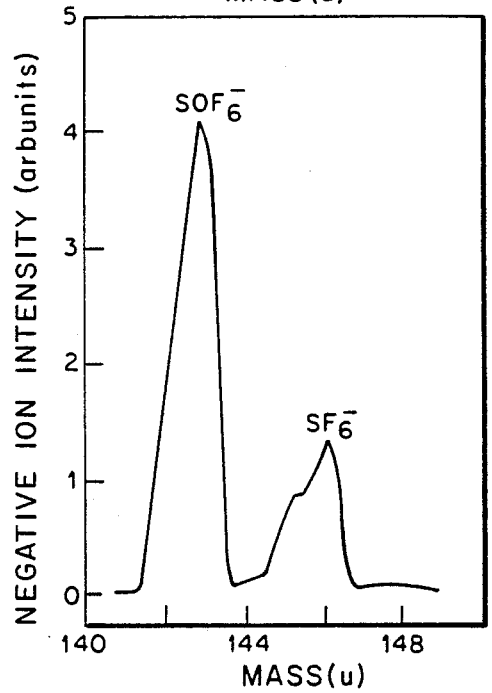
Figure 4:
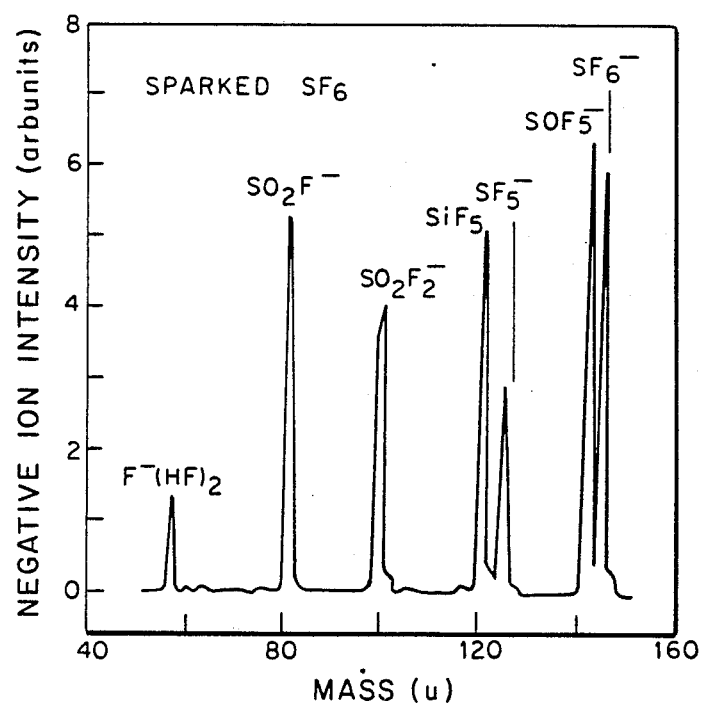
FIG. 4 is the negative ion spectrum of the sparked $SF_6$ sample of FIG. 3 using the process of the subject invention.

A demonstration of this technique was made by preparing a sparked sample of $SF_6$ and by comparing the conventional positive ion 70 eV electron impact mass spectrum FIG. 3 with the negative ion spectrum obtained by the process of this invention in FIG. 4. The $SF_6$ was sparked in a 60 cm$^3$ chamber at a pressure of 1,000 torr with a total discharge energy of 7 kJ. FIG. 3 shows the positive ion 70 eV electron impact mass spectrum of the sparked $SF_6$ sample. All the major ion peaks shown in the figure ($SF^+$, $SF_4^{++}$, $SF_2^+$, $SF_3^+$, $SF_4^+$, $SF_5^+$) are characteristic of $SF_6$. At higher sensitivity the mass spectrum shows mass peaks representing the formation of $SO_2F_2$ (m/e=83 and 102), $SiF_4$ (m/e=85), $SOF_2$ (m/e=67 and 86), and $SOF_4$ (m/e=105). The presence of the by-product $SF_4$ is not evident since its major ion peaks are at m/e=89 and 108 which are the same as for the predominant gas $SF_6$. It is clear that the by-products $SiF_4$ and $SOF_4$ are barely detectable since their ion peaks appear near very intense mass peaks. The concentrations of these by-products are listed below. They were measured by prior calibration with standards of each gas.

| By-Product | Concentration |
|---|---|
| $SOF_2$ | 3870 ppm |
| $SOF_4$ | 720 ppm |
| $SiF_4$ | 78 ppm |
| $SO_2F_2$ | 140 ppm |

Using the method described, the sample of sparked $SF_6$ was analyzed, and a mass spectrum for $P_{SF_6}=1.7$ torr, E/P 47 V cm$^2$ torr, d=1 cm is shown in FIG. 4. The spectrum shows a complete reversal of the situation of FIG. 3 in that the trace by-products dominate the spectrum rather than the major gas, $SF_6$. The by-products $SiF_4$, $SF_4$, and $SOF_4$ are indicated by the ion peaks at m/e=123, 127 and 143, respectively. The sensitive detection of $SF_4$ is particularly significant since $SF_4$ plays a central role in the formation of other long-lived by-products in $SF_6$. In addition, the by-product $SO_2$ is observed at mass 83 ($SO_2F^-$), and $SO_2F_2$ is observed at m/e=102 ($SO_2F_2^-$). Additionally, there are a series of peaks at m/e=19, 39, 59 and 79 that appear to represent the series $F^-$, $F^-(HF)$, $F^-(HF)_2$ and $F^-(HF)_3$. Thus, the mass 59 peak may be an indicator of HF formation, another by-product of sparked $SF_6$.

As illustrated by these results, the spectra produced by this invention is far superior to spectra of conventional mass spectrometry. To further enhance the sensitivity of the invention impurities can be added to the high voltage system so that the amount of by-products produced is increased without increasing the energy released in the form of electrical discharges. The inclusion of certain materials can increase production of by-products in electrical discharges by as much as two orders of magnitude (from $\sim 10^{-9}$ mole J$^{-1}$ to $10^{-7}$ mole J$^{-1}$). Examples include silicon-containing materials such as paint, lubricants and grease. Tungsten can be incorporated into the electrical material itself and will result in $WF_6$ upon electrical discharge which is detectable with high sensitivity by this technique. $WF_7^-$ is characterized by four ion peaks at m/e=315, 316, 317 and 319. Addition of small amounts of oxygen and water will lead to production of $SOF_4$, $SO_2$ and $SO_2F_2$ that are all detectable by this method as shown in FIG. 4.

In summary, this invention is a considerable improvement over prior methods of detection because it takes advantage of the high fluoride ion affinity of by-products from electrical discharges in $SF_6$ systems. The presence of the by-products signal trouble in the systems, and their affinity for fluoride enable detection by negative ion mass spectrometry that provides easily interpretable spectra at very low by-product concentration unlike conventional mass spectra. Sensitivities of 300 parts per trillion are possible using this method, an increase of about $10^4$ over previous techniques. Additionally, the ion-molecule reaction cell is simple in design and E/P (pressure reduced electric field) is easy to adjust to permit control of both the reaction time and average collision energy.

A modification that is possible is to determine the presence of the by-products based upon the time required for their negative ions to move from the cathode to the anode. Knowledge of the mobilities of the various ions could lead to the development of a device even easier to operate. The description of the preferred embodiment has been presented to explain the invention and enable others skilled in the art to best utilize it in a particular application. Obviously, many modifications are possible and one versed in the art will be able to determine the most suitable process conditions for any given set of circumstances without resorting to undue experimentation.

I claim:

1. A process for detecting by-products from electrically induced degradation of $SF_6$ in high voltage systems comprising:

at a pressure within said reaction cell sufficient to cause electron attachment to $SF_6$, placing an $SF_6$ gas to be tested in an ion-molecule reaction cell having a cathode at a first end, an anode opposite said cathode at a second end, a pin hole aperture incorporated into said anode that opens into a negative ion mass spectrometer that is at a lower pressure than is said reaction cell;

producing thermal electrons at said cathode thereby ionizing molecules of said $SF_6$ gas in the vicinity of said cathode to form $SF_6^-$ ions;

applying an electrical field in said reaction cell to induce the transfer of said $SF_6^-$ ions from said cathode to said anode resulting in the formation of by-product ions from intervening by-product molecules having a high affinity for fluoride ions;

introducing a combination of said $SF_6^-$ ions and said by-product ions into said pin hole aperture thereby effecting flow of said combination of ions from said reaction cell to said negative ion mass spectrometer; and detecting said by-product ions using negative ion mass spectrometry techniques.

2. The process of claim 1 wherein said pressure within said reaction cell is not less than 0.1 torr.

* * * * *